(12) United States Patent
Khalid et al.

(10) Patent No.: US 11,741,404 B2
(45) Date of Patent: Aug. 29, 2023

(54) METHODS AND SYSTEMS FOR USER INTERFACE INTERACTION

(71) Applicant: McKESSON CORPORATION, Irving, TX (US)

(72) Inventors: Umair Khalid, Humble, TX (US); Vijay Kumar Ravula, Gilbert, AZ (US); Jenna Fessler, Scottsdale, AZ (US); Varun Reddy Penna, Tempe, AZ (US); Adil Sameer, Gilbert, AZ (US); Harsha Chaitanya Katkam, Chandler, AZ (US); Rajat Sharma, Scottsdale, AZ (US)

(73) Assignee: McKesson Corporation, Irving, TX (US)

( * ) Notice: Subject to any disclaimer, the term of this patent is extended or adjusted under 35 U.S.C. 154(b) by 359 days.

(21) Appl. No.: 16/674,941

(22) Filed: Nov. 5, 2019

(65) Prior Publication Data
US 2021/0133652 A1 May 6, 2021

(51) Int. Cl.
G06F 17/00 (2019.01)
G06Q 10/0631 (2023.01)
G06F 40/205 (2020.01)
G06F 40/174 (2020.01)
G16H 15/00 (2018.01)

(52) U.S. Cl.
CPC ..... *G06Q 10/06311* (2013.01); *G06F 40/174* (2020.01); *G06F 40/205* (2020.01); *G16H 15/00* (2018.01)

(58) Field of Classification Search
CPC ............. G06Q 10/06311; G16H 15/00; G06F 40/205; G06F 40/174
See application file for complete search history.

(56) References Cited

U.S. PATENT DOCUMENTS

| | | | | |
|---|---|---|---|---|
| 9,192,330 B2 * | 11/2015 | Lin | ........................ | A61B 5/742 |
| D900,126 S * | 10/2020 | Trepetch | ...................... | D14/485 |
| 10,812,627 B2 * | 10/2020 | Berg | .................. | G06F 11/3438 |
| 10,977,058 B2 * | 4/2021 | Berg | .................. | G06F 9/45512 |
| D918,932 S * | 5/2021 | Gkanatsios | .................. | D14/485 |
| 11,048,793 B2 * | 6/2021 | Toth | ....................... | G06N 20/00 |
| 11,087,081 B1 * | 8/2021 | Srivastava | ............ | G06F 40/169 |
| 11,093,462 B1 * | 8/2021 | Rabbani | ................ | G06F 16/215 |
| 11,103,422 B2 * | 8/2021 | Banov | ............... | A61M 15/0065 |
| D934,890 S * | 11/2021 | Gkanatsios | .................. | D14/485 |
| 11,238,223 B2 * | 2/2022 | Nuolf | ........................ | G06F 8/33 |
| 2011/0172743 A1 * | 7/2011 | Davis | ................. | A61N 1/36535 340/573.7 |
| 2011/0246216 A1 * | 10/2011 | Agrawal | ................ | G16H 40/20 705/2 |
| 2018/0314798 A1 * | 11/2018 | Hernandez | ............. | G16H 50/30 |
| 2018/0315499 A1 * | 11/2018 | Appelbaum | ........... | G16H 20/70 |
| 2019/0155894 A1 * | 5/2019 | Gandhi | ................. | G06F 40/106 |
| 2019/0392937 A1 * | 12/2019 | Mensinger | ............. | G16H 40/67 |
| 2020/0152304 A1 * | 5/2020 | Chang | ..................... | G10L 25/63 |
| 2020/0184065 A1 * | 6/2020 | Toth | ........................ | G06F 21/31 |
| 2020/0279623 A1 * | 9/2020 | Ozeran | .................. | G16H 10/60 |
| 2020/0372990 A1 * | 11/2020 | Ho | ......................... | A61B 5/742 |
| 2021/0020318 A1 * | 1/2021 | Movassaghi | ........... | G16H 40/67 |

* cited by examiner

*Primary Examiner* — Mohammed H Zuberi
(74) *Attorney, Agent, or Firm* — Ballard Spahr LLP

(57) ABSTRACT

A configuration architecture is described. The configuration architecture may be in communication with a task management application to efficiently generate customized programs.

20 Claims, 14 Drawing Sheets

| Program | Service | Stage | Activity | Action | Rule | UI Details |
|---------|---------|-------|----------|--------|------|------------|
| Cosentyx | Intake | Benefits Investigation | Call Payor | Create Intake | | {"form Name":"Cosentyx","record IDs":{"Account":"","Case":"","Insurance___c":"","Diagnosis___c":""},"formGen":{"screens":[{"sections":[{"name":"Patient information","grid":{"size":12,"order":1},"editable":true,"fields":[{"display":"","type":"checkBoxGroup","displayType":"check |
| Cosentyx | Reimbursement | Fax Intake | Data Entry | Create Reimbursement | | {"formName":"Cosentyx","recordIds":{"Account":"","Case":"","Insurance___c":"","Diagnosis___c":""},"formGen":{"screens":[{"sections":[{"name":"Patient information","grid":{"size":12,"order":1},"editable":true,"fields":[{"display":"","type":"checkBoxGroup","displayType":"check |

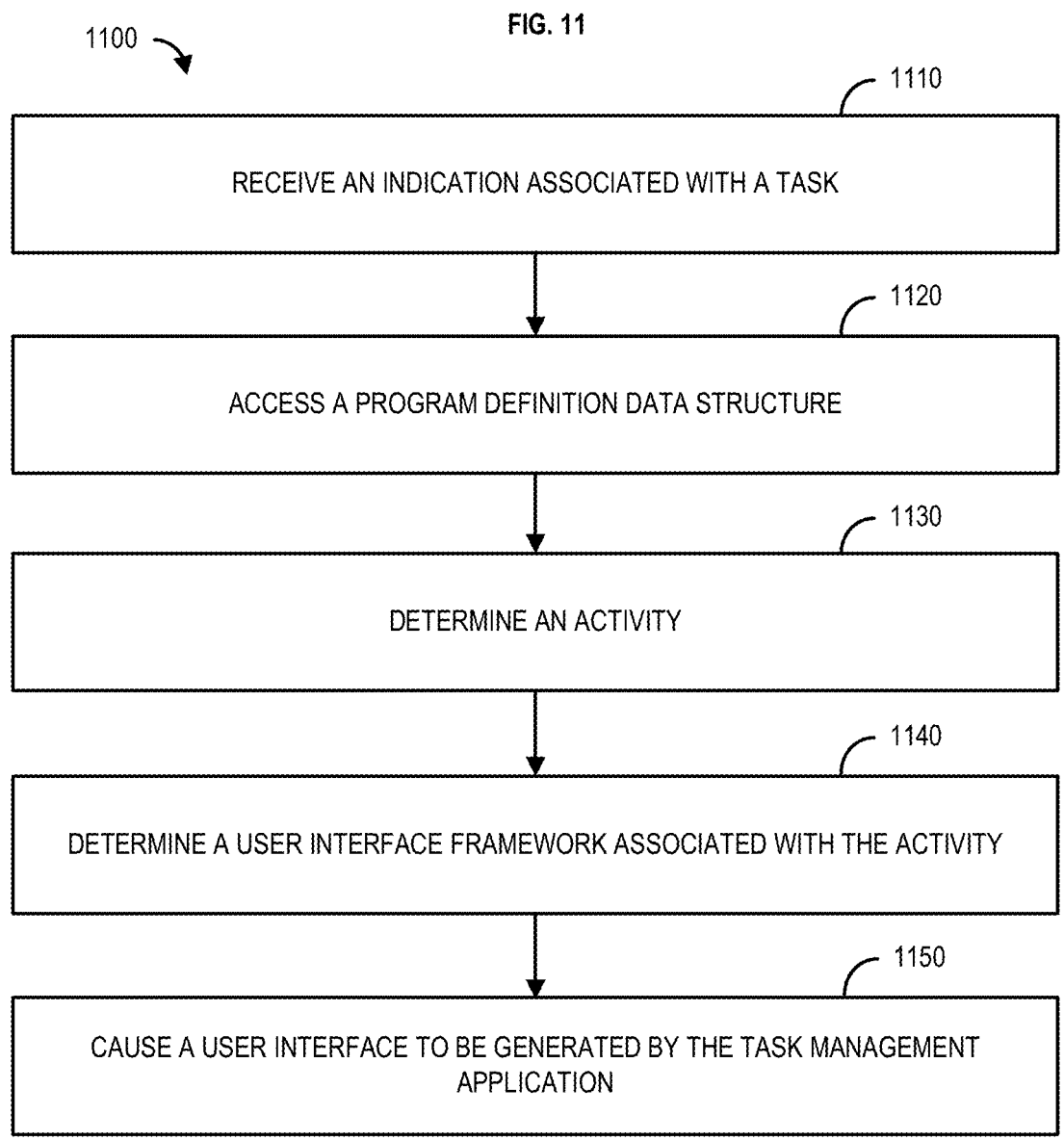

METHODS AND SYSTEMS FOR USER INTERFACE INTERACTION

BACKGROUND

In the field of specialty medicine, no two therapies are the same. And when it comes to patient support services for those therapies, the industry demands even more customized solutions. This results in expensive and overall complex systems with extremely long implementations. Additionally, overall customer satisfaction is impacted with delays in launching new patient support programs, which impacts patient's access to therapy. Furthermore, the existing patient support programs lack the intelligence/automation to determine the next best action and heavily rely on the user to make a determination which can result in human error and longer turn-around times. These and other shortcomings are addressed herein.

SUMMARY

In an aspect, methods are disclosed comprising receiving, from a task management application, an indication associated with a task, accessing, based on the indication, a program definition data structure, determining, based on the program definition data structure, an activity, determining, based on the program definition data structure, a user interface framework associated with the activity, and causing, based on the user interface framework, a user interface to be generated by the task management application.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

To easily identify the discussion of any particular element or act, the most significant digit or digits in a reference number refer to the figure number in which that element is first introduced.

FIG. 4 illustrates an example input file.
FIG. 11 illustrates an example method.

DETAILED DESCRIPTION

Figure 1:
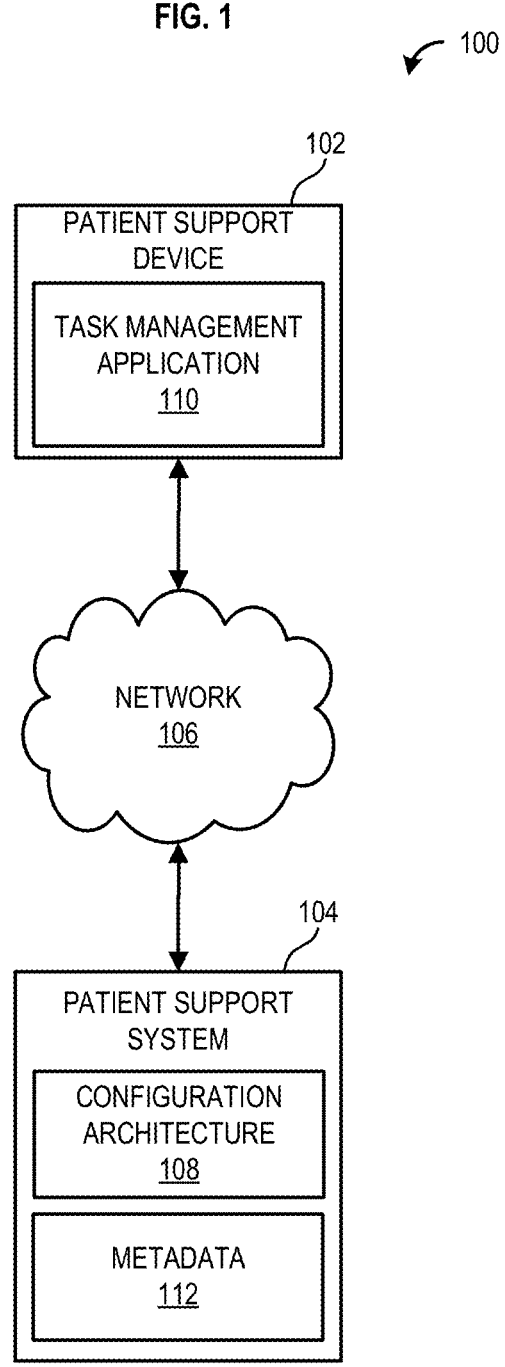
FIG. 1 illustrates an example system architecture.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Patient support programs (PSP) generally interact with one or more databases for storage of patient and physician profiles, enable completion of PSP forms (e.g., enrollment, reimbursement, etc.), enable printing of mailing labels needed for submission of PSP applications, enable printing of prescriptions that accompany PSP applications, tracking of PSP application status, and/or reminders to submit refill requests and to reapply to one or more programs when appropriate. The methods and systems described may be used for onboarding of new customized patient support programs using a proprietary, intuitive and seamless data-driven technique in a scalable system without the need to write complex code. The methods and systems described minimize the number of clicks by a user to complete a given task by allowing dynamic and configurable interfaces, rules, and intelligent automated actions. The system design is extensible enough that it not only successfully fulfills the current business needs of patient support programs but may be used for other programs. The present disclosure uses patient support programs as an example, but the methods and systems described are applicable to any type of program.

FIG. 1 is a block diagram depicting non-limiting examples of a system 100 comprising a patient support device 102 and a patient support system 104 connected through a network 106. The patient support system 104 can comprise one or multiple computers configured to operate a configuration architecture 108. The patient support system 104 can comprise for example, a computing device such as a server. The patient support device 102 can comprise one or multiple computers configured to operate a task management application 110. The patient support device 102 can comprise for example, a laptop computer, a desktop computer, a mobile phone (e.g., smartphone), a tablet, and the like. Although in FIG. 1 only a single patient support device 102 and patient support system 104 are shown, in accordance with some embodiments, the patient support system 104 can support the simultaneous use of multiple patient support devices, and the patient support device can simultaneously access multiple patient support systems.

Multiple patient support devices 102 can connect to the patient support system 104 through the network 106 such as, for example, the Internet. The network 106 is an electronic communication network that facilitates communication between the patient support device 102 and the patient support system 104. An electronic communication network includes a set of computing devices and links between the computing devices. The computing devices in the network use the links to enable communication among the computing devices in the network. The network 106 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices. In various embodiments, the network 106 includes various types of links. For example, the network 106 can include wired and/or wireless links, including BLUETOOTH, ultra-wideband (UWB), 802.11/b/g/n/ac, ZIGBEE, cellular, and other types of wireless links. Furthermore, in various embodiments, the network 106 is implemented at various scales. For example, the network 106 can be implemented as one or more local area networks (LANs), metropolitan area networks, subnets, wide area networks (such as the Internet), or can be implemented at another scale. Further, in some embodiments, the network 106 includes multiple networks, which may be of the same type or of multiple different types.

A user of the patient support device 102 may connect to the configuration architecture 108 with the task management application 110. In an aspect, the configuration architecture 108 may be resident within the task management application 110. The task management application 110 can be, for example, a software program such as that provided by SalesForce.com, Veeva, Microsoft Dynamics, Pega Software, Oracle CX, and the like. The configuration architecture 108 may be configured to provide data and/or commands to the task management application 110 to control a behavior of the task management application 110.

The patient support device 102 operates to store data and instructions. In some embodiments, the patient support device 102 stores data and instructions for the task management application 110. The task management application 110 may be configured to interface with the configuration architecture 108 through an application programming interface (API) in order to send and/or receive data to/from the configuration architecture 108. In some embodiments, the task management application 110 may be configured as a patient support program. The task management application 110 may be configured to enable one or more functions of the patient support program, including, for example, patient intake, patient data modification, and prescription support services. By way of example, for a patient intake function, an agent may be asked to perform certain tasks such as "Perform Data Entry," "Make follow up call." "Update Patient Demographics," and the like. A task may be single purpose and begin with a verb.

The patient support system 104 comprises one or more computing devices and operates to receive and/or provide data and/or commands to the patient support devices 102. The patient support system 104 may be provided by multiple redundant servers located in multiple geographic locations. In some embodiments, the patient support system 104 stores data and instructions for the configuration architecture 108. The configuration architecture 108 may be configured to interface with the task management application 110 through the API in order to send and/or receive data to/from the task management application 110. In some embodiments, the patient support system 104 stores program configuration metadata 112. The program configuration metadata 112 may define one or more program rules, data capture requirements, routing mechanics, automated actions, and the like. The program configuration metadata 112 enables a program to be onboarded into the platform. The program configuration metadata 112 may include disable/add stages, disable/add activities, disable/add actions, disable/add page, disable/add sections, disable/add fields, disable/add pick-lists, disable/add suites and the like and combinations thereof.

In some embodiments, the configuration architecture 108 may be configured to interface with a patient support program. The configuration architecture 108 may be configured as a scalable, reliable, maintainable, and extensible solution which can support a multitude of customized patient support programs while adhering to high performance standards. The configuration architecture 108 represents a data-driven approach to support efficient patient services program onboarding at reduced cost. The configuration architecture 108 allows a patient support program (e.g., the task management application 110) and associated attributes to be created via a user friendly interface. For example, the patient support program may be defined by a Microsoft Excel file which can be filled out by a business user with minimal technical knowledge. In order to archive the flexibility, scalability and future needs of different patient support programs, the configuration architecture 108 is designed to be extensible as new use cases emerge, while fully supporting current business needs. The configuration architecture 108 allows the definition of dynamic parallel business process workflows, business rules, dynamic user interfaces and system actions for patient support programs. The configuration architecture 108 design complements the task management application platform capabilities with advanced capabilities to enhance agent experience and drive end-to-end automation.

Figure 2:
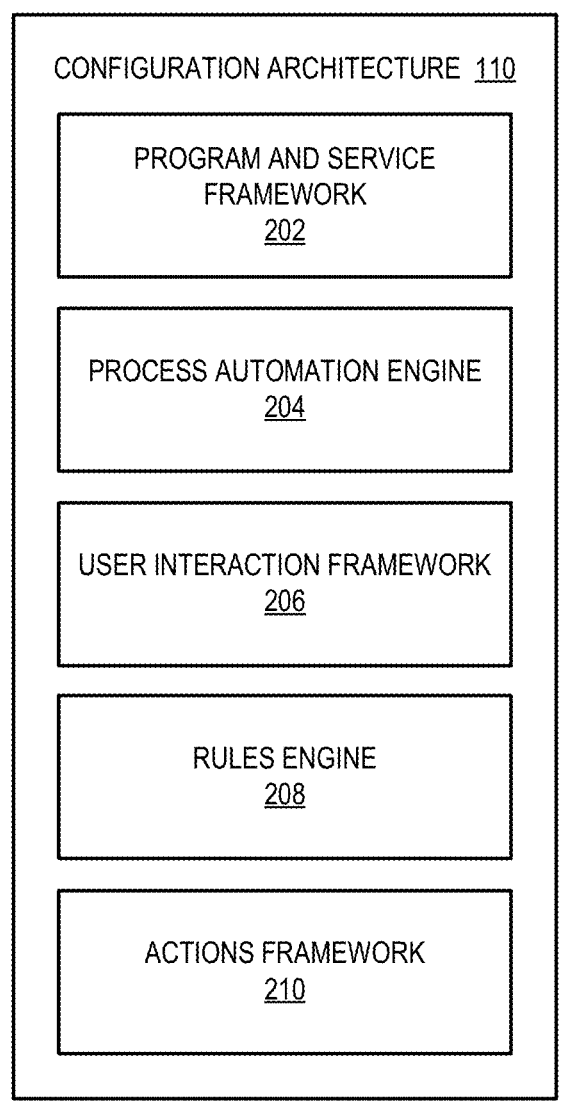
FIG. 2 illustrates an example configuration architecture.

FIG. 2 is a block diagram depicting an example view of the configuration architecture 108. The configuration architecture 108 may comprise one or more of, a program and service framework 202, a process automation engine 204, a user interaction framework 206, a rules engine 208, and an actions framework 210.

The program and service framework 202 may be configured to permit the definition of a program and a service. The program and service framework 202 may be configured to receive one or more inputs from a user. The one or more inputs from the user may be embodied in an input file, such as a Microsoft Excel file. The one or more inputs from the user may be embodied in any other form, such as a flat file, a form, and the like. The program may be related to support for a particular therapy (e.g., drug). The service may be related to patient acquisition and/or usage of the therapy. For example, the service may be a new patient intake service, for enrolling a new patient into the program. By way of further example, the service may be a reimbursement service, for providing a financial reimbursement to a patient for the purchase of the therapy. The program and service framework 202 allows the definition of metadata (e.g., the program configuration metadata 112) associated with the therapy, any global program rules, ICD codes, and different administrative types. The program and service framework 202 may also include a user interface which allows the definition of the meta-data for the entire configuration architecture.

The process automation engine 204 may be configured to manage interactions between the user interaction framework 206, the rules engine 208, the actions framework 210, and the metadata 112. The process automation engine 204 may be configured to orchestrate the engagement between the other frameworks and serve as the "glue" that binds the configuration architecture 108 together. The process automation engine 204 may be configured for a stage. For example, the process automation engine 204 may be configured to manage a fax intake. The process automation engine 204 may be configured to manage an activity. For example, the process automation engine 204 may be configured to manage an intake data entry. The process automation engine may be configured to manage a benefits investigation. Further, the process automation engine may be configured to call a payer.

The user interaction framework 206 may be a configured to cause the generation of user interfaces and forms for an activity. The user interaction framework 206 may be configured to generate dynamic purpose built user interfaces which can be rendered for each stage-action combination. The user interaction framework 206 may be metadata driven which allows rapid program based customization without needing a developer to modify any code.

The rules engine 208 may be configured as a run-time decision making platform that allows for adjustments to processes, user interactions, and actions based on pre-defined rules. The rules engine 208 may be configured to perform a decision making function throughout the application workflow. The rules engine 208 may be used to validate data provided by the user, determine if the current stage-activity is completed, determines what actions should be fired, and which next set of activities should be trigged. The rules engine 208 may be configured to execute rules. For example, the rules engine may be configured to execute a data validation rule. The rules engine 208 may be configured to access a table. For example, the rules engine 208 may be configured to access an actions decision table. The actions decision table may comprise values and decisions. For example, the actions decision table may comprise yes or no values. For example, the actions decision table may comprise decisions such as create an incomplete fax record, create an incomplete fax record, go to process decision table and the like and combinations thereof. For example, the rules engine 208 may be configured to setup a new rule to skip a "Prior Authorization" stage for a "<Brand> Connect" program when the government provides insurance. The rules engine 208 may be configured to access a process decision table. The process decision table may comprise values and/or decisions. For example, values may comprise a yes value, a no value, reimbursement value, PAP value, copay value, adherence value and the like and combinations thereof. For example, decisions may comprise a close intake data entry activity, update status of fax intake stage to pending info, close intake data entry activity, close intake data entry stage, close intake service, create reimbursement service record, create PAP service record, create copay service record, create adherence service record and the like and combinations thereof. The rules engine 208 may be configured to generate one or more messages. For example, the rules engine 208 may be configured to generate a success message. In another example, the rules engine 208 may be configured to generate an error message.

The actions framework 210 may be configured to cause execution of system actions which may be engaged based on a transition associated with stages and/or activities. The actions framework 210 may be configured to enable reusable system automations which can be referenced in the program configuration metadata 112 and may be triggered during the transition process or relying on user click events on the user interface. Examples include sending a Fax to a Health Care Provider, Sending an Email, Creating a Record, Making API calls to vendors etc. For example, the action framework 210 may execute different actions once a "Benefit Investigation" is completed.

Figure 3:
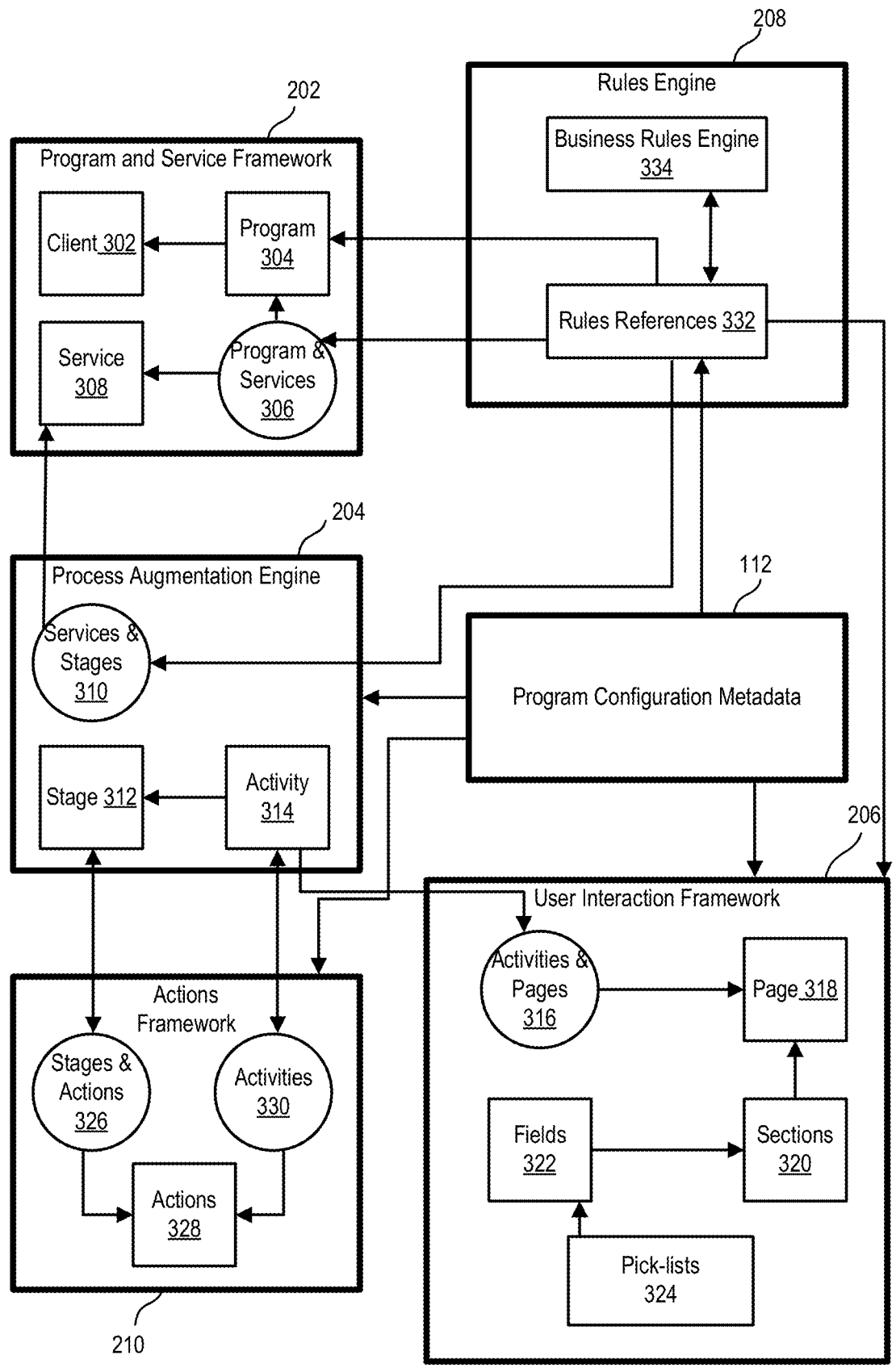
FIG. 3 illustrates an example configuration architecture.

FIG. 3 is a block diagram depicting an example view of the various components of the configuration architecture 108 and relationships of the various components of the configuration architecture 108. The program and service framework 202 may comprise a client 302, a program 304, a program and services 306, and a service 308. The client 302 may be a software program, such as the task management application 110. The program 304 may be related to support for a particular therapy (e.g., drug). The program and services 306 may be an indication of association between a program(s) and a service(s). The service 308 may be related to patient acquisition and/or usage of the therapy.

The process automation engine 204 may comprise a stages data structure 312 and an activities data structure 314. The stages data structure 312 may be an indication of one or more stages. The activities data structure 314 may be an indication of one or more activities. The service 308 may have a one to many relationship with data stored in a services and stages data structure 310. A service 308 may have at-least one stage 312 and a stage 312 may have at-least one activity 314 to be considered valid. The data structures and application logic described herein work in conjunction to support workflow progression of a service. By way of example, a service 308 may be "Reimbursement," a stage 312 may be "Intake," and an activity 314 may be "Perform Fax Data Entry."

The user interaction framework 206 may comprise a page data structure 318, a sections data structure 320, a fields data structure 322, and a pick-lists data structure 324. The page data structure 318 may be an indication of associated with one or more user interfaces (e.g., pages) including, for example, the layout and organization of buttons, fields, s-controls, custom links, and related lists on object record pages. The sections data structure 320 may be an indication of one or more areas within a page that may be used to break up the page and keep specified fields grouped together. The sections data structure 320 may indicate areas such as FormGen, page layouts, custom lighting components and the like and combinations thereof. The fields data structure 322 may be an indication of one or more fields of a user interface, including, for example, which fields are visible, read only, and/or required. The pick-lists data structure 324 may be an indication of suggested values for a field. The activities data structure 314 may have a one to one relationship with data stored in an activities and pages data structure 310. Based on the stage 312 a process is currently on, an Activity 314 is rendered for the user to provide input. The transactional data may be captured in the stage 312 record (if the relationship is 1 to 1) or a custom child object (if relationship if 1 to many) as the child object of the stage 312. The activity 314 record may be configured to track a start date and an end date of the activity 314 along with other Key Performance Indicators (KPIs).

The actions framework 210 may comprise an actions data structure 328. The actions data structure 328 may be an indication of one or more actions that may be executed. The actions data structure 328 may have a one to many relationship with data stored in a stages and actions data structure 326 and a one to many relationship with data stored in a stages and activities data structure 330. A stage 312 and/or activity 314 can be associated to one or many actions 328. These actions 328 can be executed during entry and/or exit of a Stage/Activity. Actions 328 can also be user triggered, based on an association with the stage 312 and/or a type of user interface action.

The rules engine 208 may comprise a rule references data structure 332 and a business rules engine 334. The rule references data structure 332 may be an indication of one or more rules. The business rules engine 334 may be configured to act or otherwise enforce the one or more rules. The business rules engine 334 may be configured to act or otherwise enforce rules such as next step/page, field(s) to show/hide, field(s) validations, eligibility rules and the like and combinations thereof. The rule references data structure 332 may have a many to one relationship with each of the program 304, the program and services data structure 306, the services and stages data structure 310, and the user interaction framework 206. Rules can be associated with a service 308 and/or a stage 312 and/or an activity 314 and/or an action 328. Rules may be categorized, for example, as entry rules, exit rules, validation rules, eligibility rules, and the like. By way of example, if an entry rule is evaluated as true, then the associated service 308, stage 312, or activity 314 can become active. Similarly, if an exit rule is evaluated as false, the associated service 308, stage 312, or activity 314 will be determined to be not completed.

FIG. 4 shows an example input file 400 associated with the program and service framework 202. The input file 400 may comprise one or more tables. As shown, the input file 400 comprises a single table. The Program column indicates a therapy for which the patient support program is to be generated. The Service column indicates a service associated with patient acquisition of the therapy. The Stage column indicates a stage associated with completion of the service. The Activity column indicates an activity associated with completion of the stage. The Action column indicates an action necessary for the activity. The Rule column indicates one or more rules to be applied to the patient support program. The UI Details column indicates how a user interface for the action should be generated and/or displayed. The UI Details column may be auto-generated by the system based on user inputs into a program setup interface. The program setup interface may be used to define the services, stages, and/or activities for a particular program. The program setup interface may be used to define rules, any actions, and the UI details. The UI details may be defined by selecting a database table and field, a user-friendly label for that field, field placement in the screen, any validation rules (required, phone number, etc,), and pick-lists. Once defined, the resulting configuration may be compiled into a JSON data structure and then populated in the input file 400.

Figure 5:
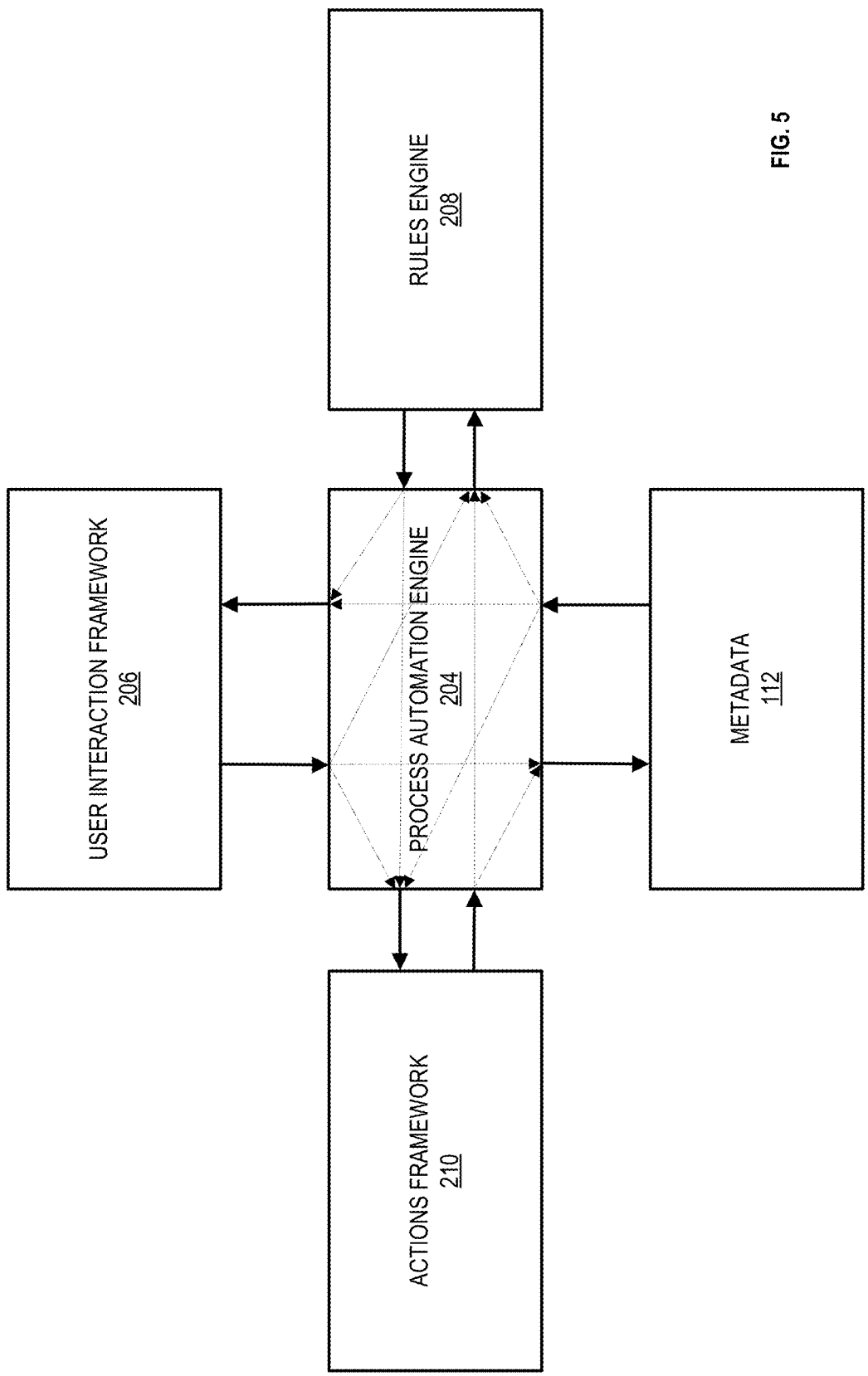
FIG. 5 illustrates an example automation engine.

FIG. 5 is a block diagram depicting an example view of the process automation engine 204. The process automation engine 204 supports a self-adjusting parallel business workflow as a state machine. The process automation engine 204 may be configured to determine a next best action based for each case based on known data about particular scenario and rules defined in the rules engine 208. The process automation engine 204 eliminates the needs for a user to determine the next action and drives outcomes in the most optimized manner. The process automation engine 204 supports parallel steps to take place while keeping track of dependencies to make sure the most optimized fulfillment of the business outcome. The process automation engine 204 may manage the orchestration between the user interface framework 206, business rules engine 334, actions framework 210 and program configuration metadata 112. The process automation engine 204 may support the separation of concerns and single responsibility principle software design pattern.

The process automation engine 204 may be engaged either on a user click event or though the actions framework 210, for example, when a user clicks submit on a form or when the user initiates a new service though a "New Intake" button. The following example sequence of events may be orchestrated by the process automation engine 204 to make ensure the next best action(s) is determined. The process automation engine 204 may determine a current state of the Service/Stage/Activity combination. The process automation engine 204 may engage the user interface framework 206 to perform a "validate and save" operation. If successful, the user interface framework 206 may utilize the rules engine 208 to validate any complex data validation rules. The process automation engine 204 may then engage the rules engine 208 to run exit rules. If the "validate and save" operation is unsuccessful, validation message may be displayed and the exit rules will determine which next Stages and Activities should be setup to active. Once exit rules have been successfully executed, the actions framework 210 may be engaged to execute one or more exit actions. The exit actions may cause one or more facsimile transmissions, API calls, record creations, and the like. The process automation engine 204 may then update the status of the current Stage or Activity as completed and engage the user interface framework 206 to navigate the user to an Activity completion interface.

Figure 6:
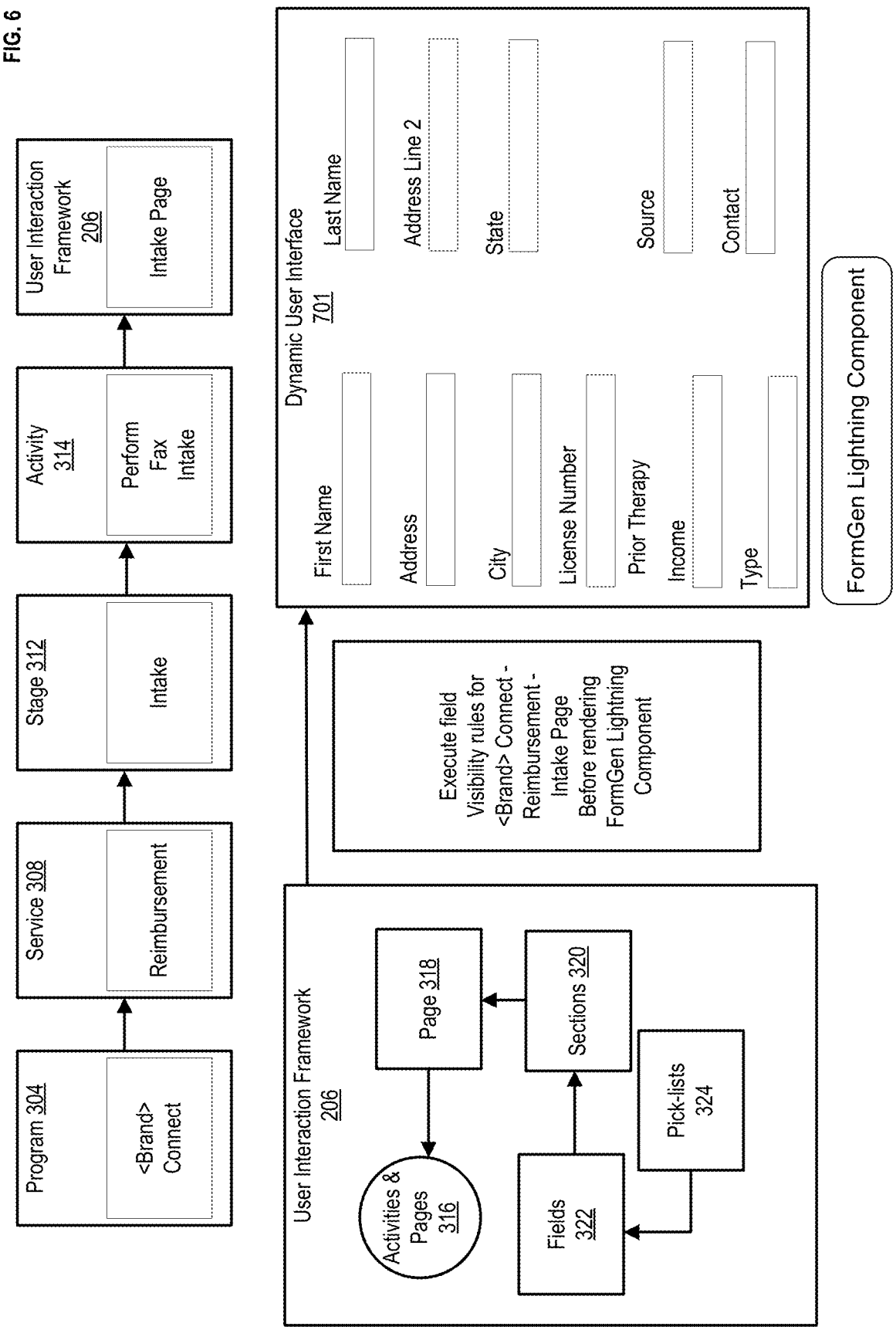
FIG. 6 illustrates a design example of a user interaction framework.

FIG. 6 shows a design example of the user interaction framework 206 in a patient support program use case where a dynamic user interface 601 is rendered for a patient intake. Dynamic user interface 601 is the result of applying a program 304 associated with service 306 at stage 312 in order to perform activity 314. Dynamic user interface 601 may be used to populate fields related to a user. For example, dynamic user interface 601 may be used to populate fields such as name, address, license numbers, income information, prior therapy, other demographic information and the like and combinations thereof.

The user interaction framework 206 is responsible for rendering dynamic user interfaces for a given Service-Stage-Activity combination for a particular program. The user interaction framework 206 may be engaged by the process automation engine 204 when a determination is made that a new user interface needs to be rendered, or when a user has clicked submit on a form. The user interaction framework 206 may be used to perform create, read, update, and delete (CRUD) operations associated with the Service-Stage-Activity combination. By way of example, when a load operation is performed the user interaction framework 206 may determine metadata for the current service-stage-activity combination including user interface details. The user interaction framework 206 may parse an associated JSON file into an object and group fields by objects, then for each object, perform SELECT queries to determine current values. The user interaction framework 206 may filter objects/fields for which the current user does not have read permissions. The user interaction framework 206 may populate values into the object and run validation rules defined for fields. The user interaction framework 206 may populate any field validation error messages into the object. The user interaction framework 206 may encode the object into JSON and return browser Javascript code. The JavaScript code may parse the JSON and loop through each defined field. The user interaction framework 206 may update a browser Document Object Model (DOM) with each field, its associated values and validation error messages.

Figure 7:
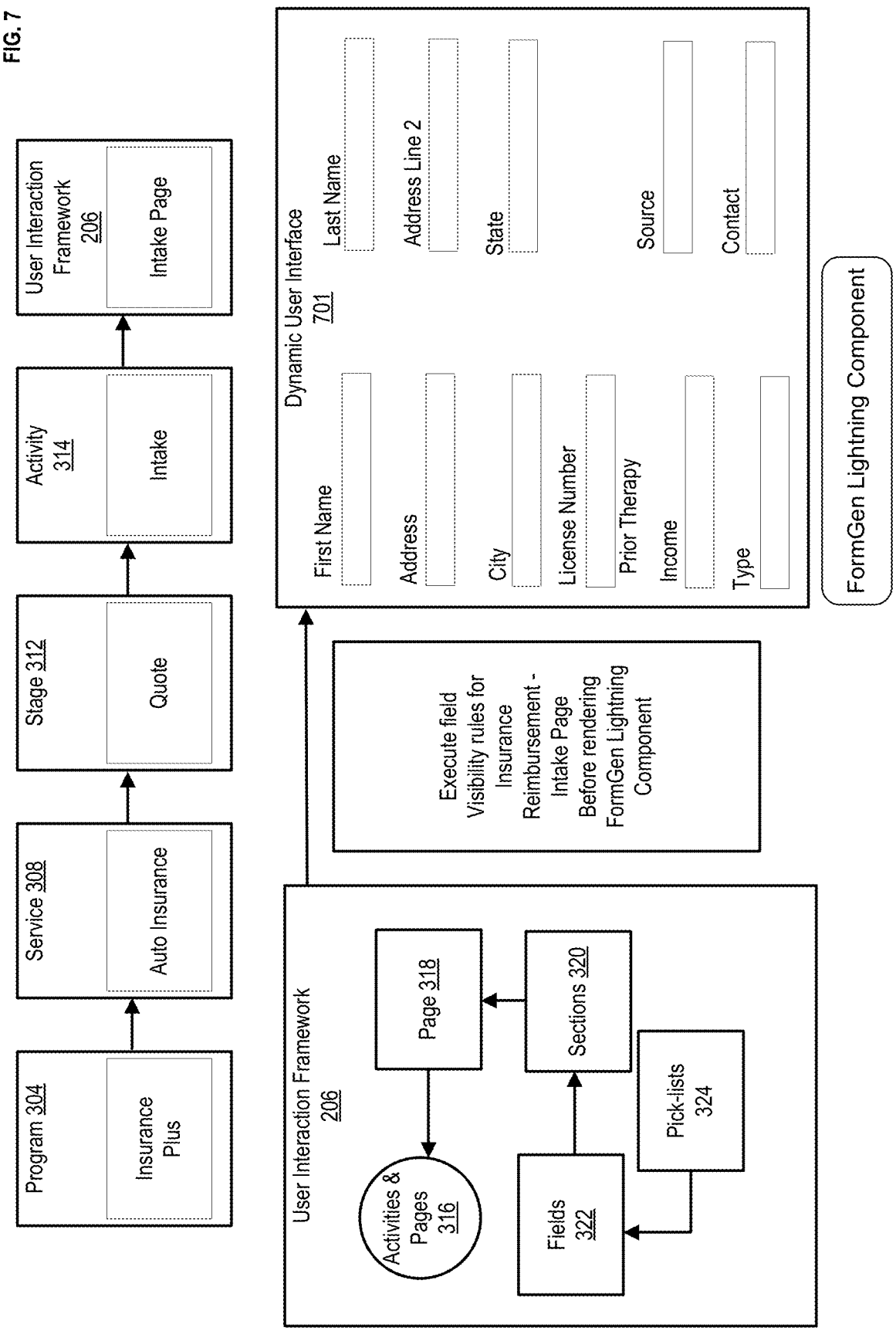
FIG. 7 illustrates a design example of a user interaction framework.

FIG. 7 shows a design example of the user interaction framework 206 in an auto insurance program use case where a dynamic user interface is rendered for a quote intake. User interaction framework 206 supports configuration driven context aware dynamic user interfaces. In order for the user interaction framework 206 an on-the-fly form generator (FormGen) is used that builds custom forms out of predefined meta-data supporting n+ objects within a single screen. Each form is fully customizable through a set of form field types. FormGen supports dynamic showing or hiding of fields, advance data validations though regular expression and field positioning using a grid-based approach. FormGen also includes functionality to create grid modules for multi-dimensional fields which can grow or shrink as needed. The elasticity of FormGen allows user interfaces to be dynamic at a form and field level—the same form may have different field requirements based on other information provided previously in the request. For use cases where a dynamic user interface for data capture is not required and the form is built for a single object, the user interaction framework 206 also supports rendering of task management application's standard page layouts for a given screen. Once the information is captured, the user interaction framework 206 utilizes a ViewGen module to display previously captured data to the user. The ViewGen module eliminates the need for users to search or open new tabs within the task management application. ViewGen has the capability to bring together data from multiple objects into a single extensible view while being configurable for each screen. This allows ViewGen to be context aware and rendered differently based on a particular step.

Figure 8:
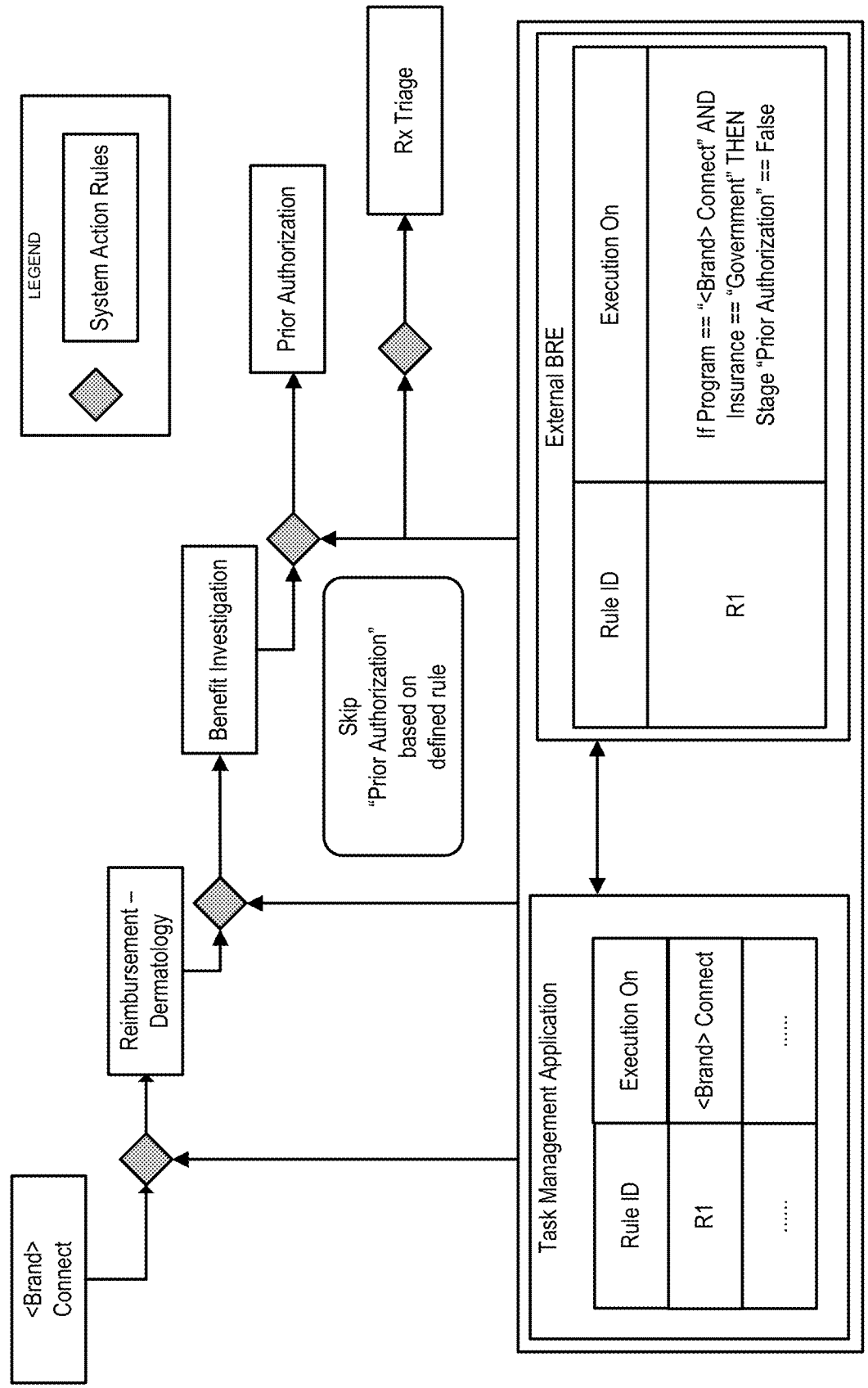
FIG. 8 illustrates an example view of a rules engine.

FIG. 8 is a block diagram depicting an example view of the rules engine 208.

The rules engine 208 supports intelligent decision-making capabilities within the configuration architecture 108. The rules engine 208 allows for offloading complex computations out of the task management application. As a result, the rules engine 208 can be utilized to overcome governor limits imposed by a multi-tenant cloud environment into a scalable PaaS. The rules engine 208 supports on the fly complex decision making by creating sophisticated models with multiple data points from the task management application and other data-sets. The rules are context aware and support multiple permutations and combination for the action which are taken after rule processing. By way of example, the rules engine 208 may be utilized for determining one or more of the following:

1. Should a patient be eligible for assistance, free drug etc.
2. How to progress though the business process for each service. This type of rule can be triggered by a user clicking save on a screen.
3. Should a certain field value be valid based on other field(s) values. This type of rule can be triggered on a user clicking save on a screen.

4. Should a certain field should be visible to the user based on other field(s) values criteria. This type of rule can be triggered before loading a screen.

Figure 9:
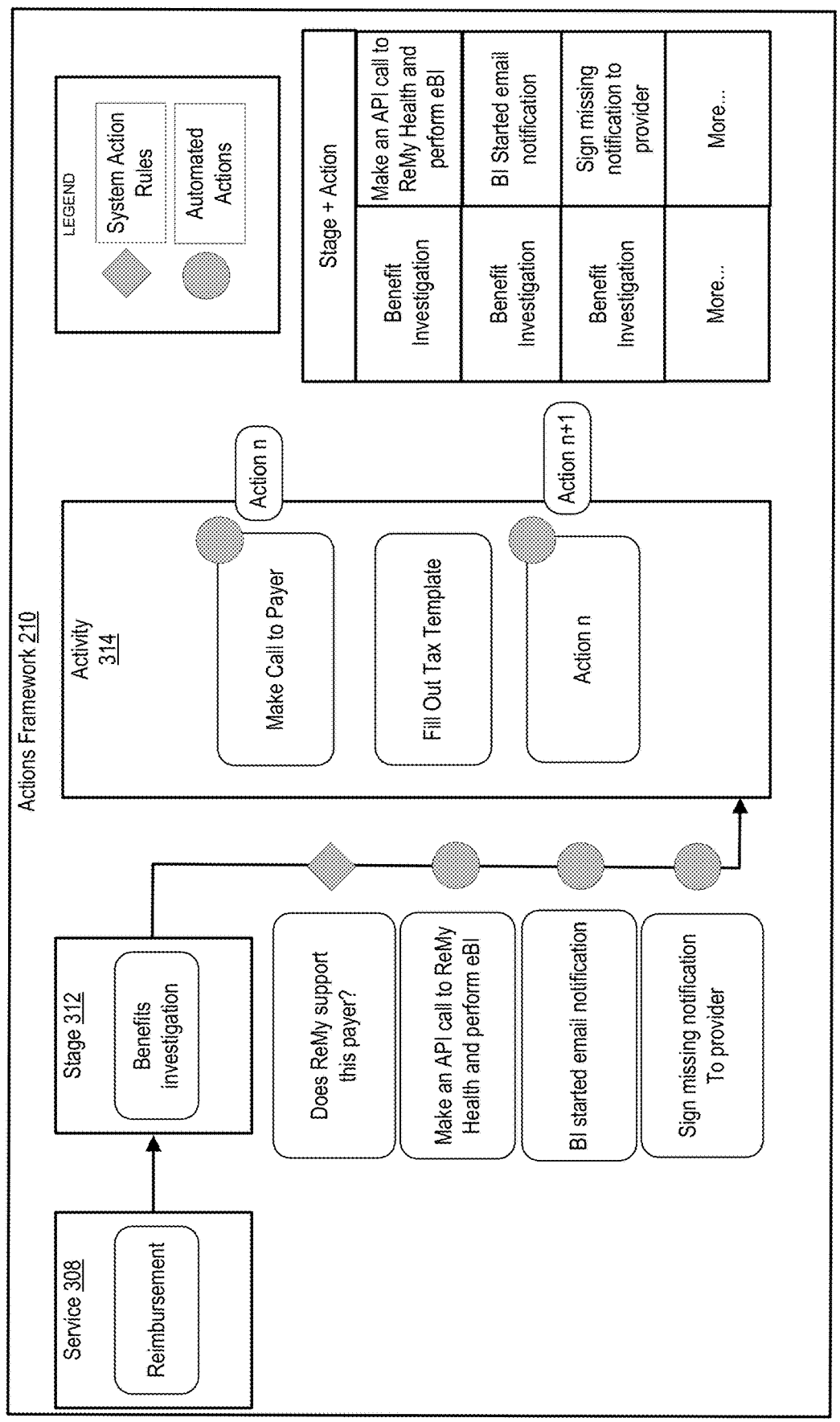
FIG. 9 illustrates a design example of an actions framework.

5. Should a certain Fax or Email or API Call should be made based on certain field(s) values criteria. This type of rule can be triggered on user clicking save on a screen FIG. 9 shows a design example of the actions framework 210 in an auto insurance program use case where system automated actions are fulfilled. The actions framework 210 allows for reusable system automations which can be referenced in the program configuration metadata 112 and may be triggered during a transition of process or in response to a user click events in a user interface. Examples include sending a Fax to a Health Care Provider, Sending an Email, Creating a Record, Making API calls to vendors etc. The actions framework 210 enables a reduction in user touch points and drives intelligent and extensive business process automation within the configuration architecture 108. The actions framework 210 supports invoking system action. For example, the actions framework 210 can invoke one or more of the following types of reusable plug and play system actions but not limited to:

1. Calling CRM automations
2. Sending Email
3. Sending Fax
4. Scheduling of future events
5. Making an API Call
6. Calling a Class The system actions can be initiated from the actions framework 210 using rule-based action filtering.

Figure 10A:
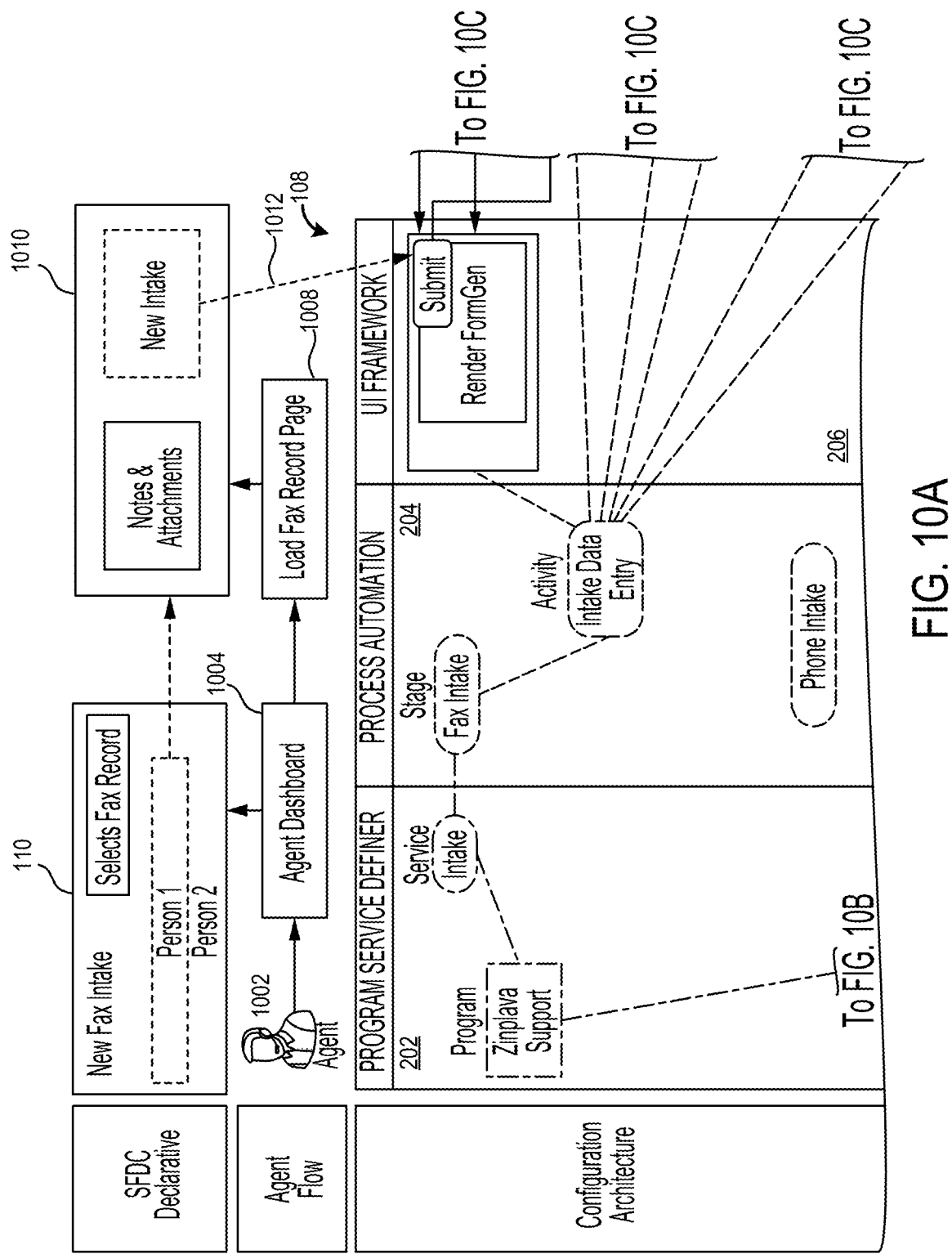
FIG. 10A illustrates an example flow of interactions between a task management application and a configuration architecture.
Figure 10B:
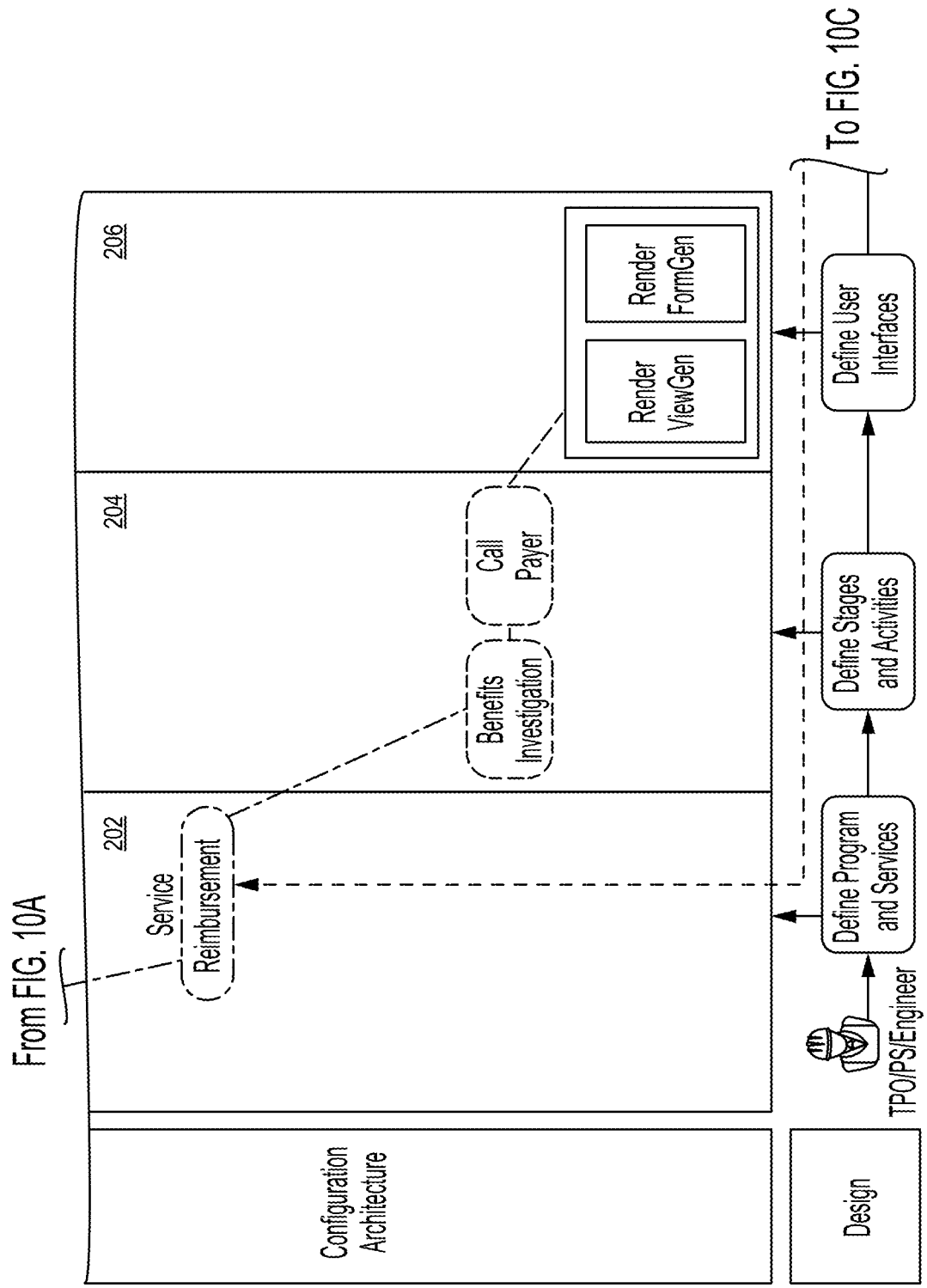
FIG. 10B illustrates an example flow of interactions between a task management application and a configuration architecture.
Figure 10C:
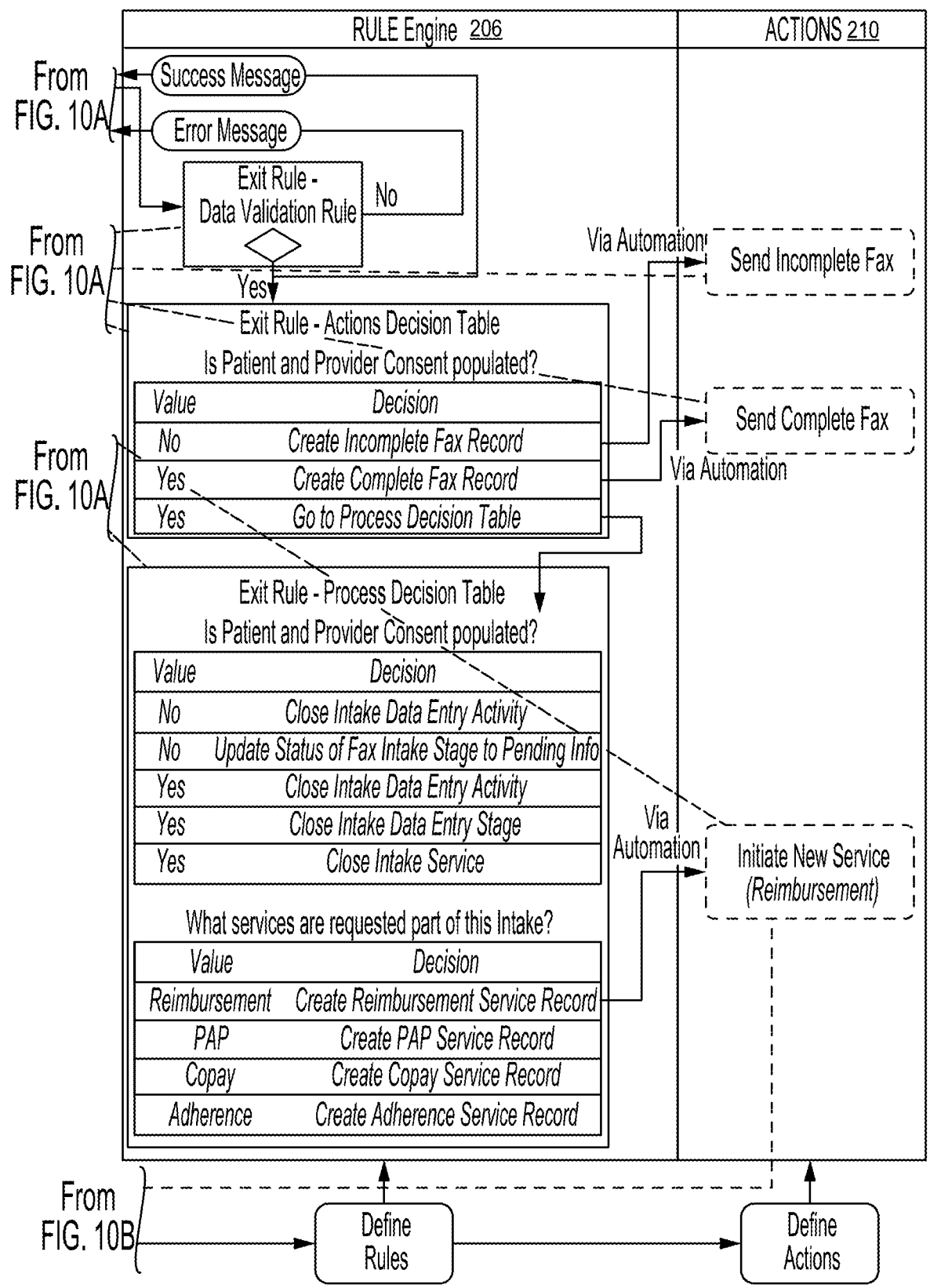
FIG. 10C illustrates an example flow of interactions between a task management application and a configuration architecture.

FIGS. 10A-10C show an example flow of the interactions between the task management application 110 and the configuration architecture 108. A user 1002 of the task management application 110 may identify a task for completion using a dashboard 1004. In the example of FIGS. 10A-10C, the user 1002 selects a "New Fax Intake" task by selecting a user interface element (e.g., button, link, etc.) associated with the task at 1008. The user 1002 may be presented with a screen 1010 that enables the user 1002 to select a user interface element associated with performing the task, e.g., "New Intake." Upon selection of the user interface element, an indication 1012 may be passed to the configuration architecture 108. The indication 1012 may comprise a string, token, symbol, or the like. The indication may identify a program, a service, a stage, and an activity. The program and service framework 202 may parse the indication to determine the program, the service, the stage, and the activity. The program and service framework 202 may access the metadata 112 to access the program, the service, the stage, and the activity associated with the indication 1012. The program and service framework 202 may pass the program, the service, the stage, and the activity to the process automation engine 204. The process automation engine 204 may utilize the program, the service, the stage, and the activity to identify an associated user interface framework 206. The user interface framework 206 may comprise data that can be used to generate a user interface (e.g., a form) associated with the activity. The user interface framework 206 may provide some or all of the data necessary for user interface generation to the task management application 110. The task management application 110 may generate the user interface based on the received data.

The user 1002 may proceed to interact with the generated user interface (e.g., fill out one or more fields of a form) and submit data back to the configuration architecture 108. The configuration architecture 108 passes the received data to the rules engine 208 to apply one or more rules to the received data. The one or more rules can comprise a data validation rule, an exit rule, and/or process rule. A data validation rule may comprise any rule related to the form/type of data that is expected to be received. For example, a social security number is expected to consist of all numbers and contain 9 digits. In the event any received data does not pass a data validation rule, the user interface framework 206 may cause an error message to be generated by the task management application 110. An exit rule may comprise any rule related to whether or not sufficient data has been received to proceed to an action and/or a process decision table. For example, the rules engine 208 may determine whether both a patient consent field and a provider consent field have been populated. If either has not been populated, then the rules engine 208 may generate an indication of an incomplete fax record and pass an indication to the actions framework 210 to send an automated message indicating that the received fax information is incomplete. If both are populated, then the rules engine 208 may generate an indication of a complete fax record, pass an indication to the actions framework 210 to send an automated message indicating that the received fax information is complete, and proceed to the process decision table. The process decision table may comprise process decision rules that govern the next step in the process based upon data received from the task management application 110. For example, the rules engine 208 may again determine whether both a patient consent and a provider consent field have been populated or pass an indication of the prior determination to the process decision table. If the determination is that either the patient consent field or the provider consent field have not been populated, then the data intake activity may be closed and a status of the fax intake may be updated to pending. If the determination is that both the patient consent field or the provider consent field have been populated, then the data intake activity may be closed, the data intake stage may be closed, and the intake service may be closed.

FIG. 11 shows an example method 1100. The method 1100 may comprise, receiving, from a task management application, an indication associated with a task at 1110. The indication can comprise a string. The task can comprise a new patient intake task or a therapy reimbursement task.

The method 1100 may comprise accessing, based on the indication, a program definition data structure at 1120. Determining, based on the indication, the activity can comprise parsing the string to determine a program, a service, a stage, and the activity. The program definition data structure can comprise an indication of a program, a service associated with the program, a stage associated with the service, and an activity associated with the stage. The program can be a therapy, the service can be associated with patient acquisition of the therapy, the stage can be associated with completion of the service, and the activity can be associated with completion of the stage.

The method 1100 may comprise determining, based on the program definition data structure, an activity at 1130.

The method 1100 may comprise determining, based on the program definition data structure, a user interface framework associated with the activity at 1140. The user interface framework can comprise one or more instructions for generation of a user interface, wherein the one or more instructions define one or more data entry fields and placement for the one or more data entry fields.

The method 1100 may comprise causing, based on the user interface framework, a user interface to be generated by the task management application at 1150. Causing, based on the user interface framework, the user interface to be generated by the task management application can comprise sending the user interface framework to the task management application.

The method 1100 may further comprise receiving, via the user interface, a submission of data, determining, based on the program definition data structure, an exit rule associated with the activity, and executing, based on the data satisfying the exit rule, one or more actions to complete the task. The exit rule can define an action decision table. The method 1100 may further comprise determining a value of the data and determining, based on the value of the data, the one or more actions from the action decision table.

Figure 12:
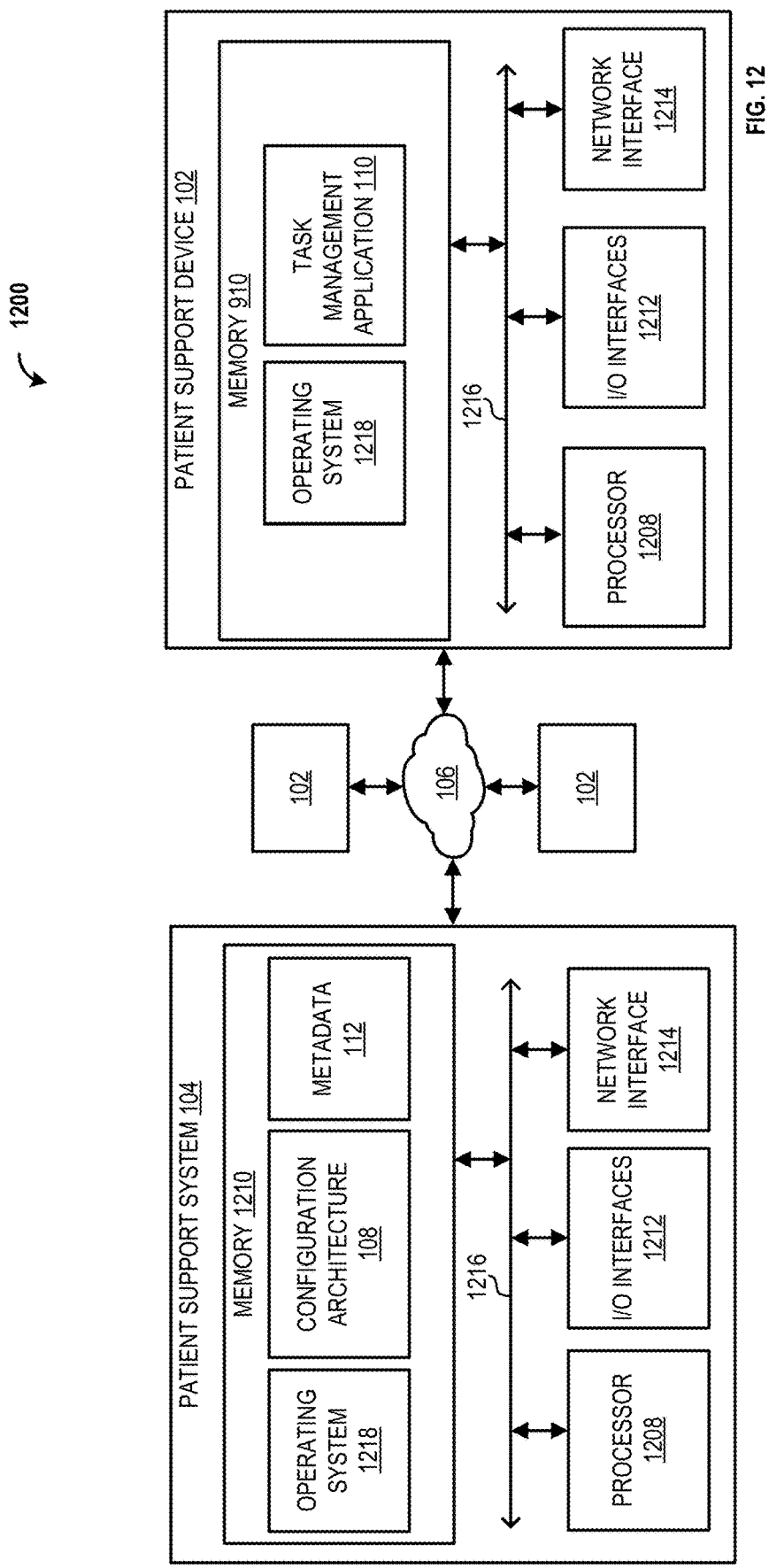
FIG. 12 illustrates an example operating environment.

FIG. 12 is a block diagram depicting an environment 1200 comprising non-limiting examples of the patient support system 104 and the patient support device 102 connected through the network 106. In an aspect, some or all steps of any described method may be performed on a computing device as described herein. The patient support system 104 can comprise one or multiple computers configured to store one or more of the configuration architecture 108, the metadata 112, and the like. The patient support device 102 can comprise one or multiple computers configured to store the task management application 110. The patient support system 104 and/or the patient support system 104 can be a computing device, such as, for example, a mobile phone, a tablet computer, a laptop computer, a desktop computer, a server, and the like. Multiple patient support devices 102 can connect to the patient support system 104 through the network 106 such as, for example, the Internet. A user on a patient support device 102 may connect to the configuration architecture 108 with the task management application 110. In an aspect, one or more of the configuration architecture 108, the metadata 112, and/or the task management application 110 may be resident on the patient support system 104, the patient support device 102, or both.

The patient support system 104 and the patient support device 102 can be a digital computer that, in terms of hardware architecture, generally includes a processor 1208, memory system 1210, input/output (I/O) interfaces 1212, and network interfaces 1214. These components (1208, 1210, 1212, and 1214) are communicatively coupled via a local interface 1216. The local interface 1216 can be, for example but not limited to, one or more buses or other wired or wireless connections, as is known in the art. The local interface 1216 can have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1208 can be a hardware device for executing software, particularly that stored in memory system 1210. The processor 1208 can be any custom made or commercially available processor, a central processing unit (CPU), an auxiliary processor among several processors associated with the patient support system 104 and the patient support device 102, a semiconductor-based microprocessor (in the form of a microchip or chip set), or generally any device for executing software instructions. When the patient support system 104 and the patient support device 102 is in operation, the processor 1208 can be configured to execute software stored within the memory system 1210, to communicate data to and from the memory system 1210, and to generally control operations of the patient support system 104 and the patient support device 102 pursuant to the software.

The I/O interfaces 1212 can be used to receive user input from and/or for providing system output to one or more devices or components. User input can be provided via, for example, a keyboard and/or a mouse. System output can be provided via a display device and a printer (not shown). I/O interfaces 1212 can include, for example, a serial port, a parallel port, a Small Computer System Interface (SCSI), an IR interface, an RF interface, and/or a universal serial bus (USB) interface.

The network interface 1214 can be used to transmit and receive from the patient support system 104 or the patient support device 102 on the network 106. The network interface 1214 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi), or any other suitable network interface device. The network interface 1214 may include address, control, and/or data connections to enable appropriate communications on the network 1204.

The memory system 1210 can include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory system 1210 may incorporate electronic, magnetic, optical, and/or other types of storage media. Note that the memory system 1210 can have a distributed architecture, where various components are situated remote from one another, but can be accessed by the processor 1208.

The software in memory system 1210 may include one or more software programs, each of which comprises an ordered listing of executable instructions for implementing logical functions. In the example of FIG. 12, the software in the memory system 1210 of the patient support system 104 can comprise the configuration architecture 108 (or subcomponents thereof), the metadata 112, and a suitable operating system (O/S) 1218. In the example of FIG. 12, the software in the memory system 1210 of the patient support device 102 can comprise the task management application 110 and a suitable operating system (O/S) 1218. The operating system 1218 essentially controls the execution of other computer programs, and provides scheduling, input-output control, file and data management, memory management, and communication control and related services.

For purposes of illustration, application programs and other executable program components such as the operating system 1218 are illustrated herein as discrete blocks, although it is recognized that such programs and components can reside at various times in different storage components of the patient support system 104 and/or the patient support device 102. An implementation of the configuration architecture 108, the metadata 112, and/or the task management application 110 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
   accessing, by a task management application, based on an indication associated with a task, a program definition data structure associated with a program;
   determining, based on the program definition data structure, a current activity of a plurality of activities associated with the program;
   determining, based on the program definition data structure, a user interface framework associated with the current activity, wherein the user interface framework defines a plurality of user interfaces that are each associated with a combination of: at least one service of a plurality of services associated with the program, at least one stage of a plurality of stages associated with the at least one service, and at least one activity of the plurality of activities associated with the at least one service;
   determining, based on the current activity, a first stage of the plurality of stages for a first service of the plurality of services associated with the program, wherein the current activity is one of the plurality of activities associated with the first service;
   selecting a first user interface of the plurality of user interfaces based on the user interface framework and a combination of: the first service, the first stage, and the current activity;
   determining, based on the user interface framework and the combination, one or more data entry fields, of a plurality of data entry fields of the first user interface, that are to be displayed via the task management application, wherein the user interface framework indicates which data entry fields of the plurality of data entry fields are to be displayed based on the combination of the first service, the first stage, and the current activity; and
   in response to determining the one or more data entry fields that are to be displayed, causing the first user interface comprising the one or more data entry fields to be displayed by the task management application, wherein the remaining data entry fields, of the plurality of data entry fields of the first user interface, are not displayed via the task management application based on the user interface framework and the combination of the first service, the first stage, and the current activity.

2. The method of claim 1, wherein the indication comprises a string, and wherein accessing, based on the indication associated with the task, the program definition data structure comprises: parsing the string to determine the program, the plurality of services, the plurality of stages, and the plurality of activities.

3. The method of claim 1, wherein the task comprises a new patient intake task or a therapy reimbursement task.

4. The method of claim 1, wherein the program is a therapy, the first service is associated with patient acquisition of the therapy, the first stage is associated with completion of the first service, and the current activity is associated with completion of the first stage.

5. The method of claim 1, wherein the user interface framework comprises one or more instructions for generation of the plurality of user interfaces, and wherein the one or more instructions define the one or more data entry fields, of the plurality of data entry fields of the first user interface, and placement for the one or more data entry fields.

6. The method of claim 1, wherein causing the first user interface to be displayed by the task management application comprises: sending the user interface framework to the task management application.

7. The method of claim 1, further comprising:
   receiving, via the first user interface, a submission of data;
   determining, based on the program definition data structure, an exit rule associated with the current activity; and
   executing, based on the data satisfying the exit rule, one or more actions to complete the task.

8. The method of claim 7, wherein the exit rule defines an action decision table.

9. The method of claim 8, further comprising:
   determining a value of the data; and
   determining, based on the value of the data, the one or more actions from the action decision table.

10. An apparatus comprising:
    one or more processors; and
    a memory storing processor-executable instructions that, when executed by the one or more processors, cause the apparatus to:

access, by a task management application, based on an indication associated with a task, a program definition data structure associated with a program;

determine, based on the program definition data structure, a current activity of a plurality of activities associated with the program;

determine, based on the program definition data structure, a user interface framework associated with the current activity, wherein the user interface framework defines a plurality of user interfaces that are each associated with a combination of: at least one service of a plurality of services associated with the program, at least one stage of a plurality of stages associated with the at least one service, and at least one activity of the plurality of activities associated with the at least one service;

determine, based on the current activity, a first stage of the plurality of stages for a first service of the plurality of services associated with the program, wherein the current activity is one of the plurality of activities associated with the first service;

select a first user interface of the plurality of user interfaces based on the user interface framework and a combination of: the first service, the first stage, and the current activity;

determine, based on the user interface framework and the combination, one or more data entry fields, of a plurality of data entry fields of the first user interface, that are to be displayed via the task management application, wherein the user interface framework indicates which data entry fields of the plurality of data entry fields are to be displayed based on the combination of the first service, the first stage, and the current activity; and in response to determining the one or more data entry fields that are to be displayed, cause the first user interface comprising the one or more data entry fields to be displayed by the task management application, wherein the remaining data entry fields, of the plurality of data entry fields of the first user interface, are not displayed via the task management application based on the user interface framework and the combination of the first service, the first stage, and the current activity.

11. The apparatus of claim 10, wherein the indication comprises a string, and wherein the processor-executable instructions that cause the apparatus to access, based on the indication associated with the task, the program definition data structure further cause the apparatus to parse the string to determine the program, the plurality of services, the plurality of stages, and the plurality of activities.

12. The apparatus of claim 10, wherein the task comprises a new patient intake task or a therapy reimbursement task.

13. The apparatus of claim 10, wherein the program is a therapy, the first service is associated with patient acquisition of the therapy, the first stage is associated with completion of the first service, and the current activity is associated with completion of the first stage.

14. The apparatus of claim 10, wherein the user interface framework comprises one or more instructions for generation of the plurality of user interfaces, and wherein the one or more instructions define the one or more data entry fields, of the plurality of data entry fields of the first user interface, and placement for the one or more data entry fields.

15. The apparatus of claim 10, wherein the processor-executable instructions that cause the apparatus to cause the first user interface to be displayed by the task management application further cause the apparatus to send the user interface framework to the task management application.

16. The apparatus of claim 10, wherein the processor-executable instructions further cause the apparatus to:

receive, via the first user interface, a submission of data;

determine, based on the program definition data structure, an exit rule associated with the current activity; and execute, based on the data satisfying the exit rule, one or more actions to complete the task.

17. The apparatus of claim 16, wherein the exit rule defines an action decision table.

18. The apparatus of claim 17, further comprising processor-executable instructions that, when executed by the one or more processors cause the apparatus to:

determine a value of the data; and determine, based on the value of the data, the one or more actions from the action decision table.

19. A system comprising:

a first computing device configured to: generate, by a task management application, an indication associated with a task; and a second computing device, in communication with the first computing device, configured to:

receive, from the task management application, the indication associated with the task;

access, based on the indication, a program definition data structure associated with a program;

determine, based on the program definition data structure, a current activity of a plurality of activities associated with the program;

determine, based on the program definition data structure, a user interface framework associated with the current activity, wherein the user interface framework defines a plurality of user interfaces that are each associated with a combination of: at least one service of a plurality of services associated with the program, at least one stage of a plurality of stages associated with the at least one service, and at least one activity of the plurality of activities associated with the at least one service;

determine, based on the current activity, a first stage of the plurality of stages for a first service of the plurality of services associated with the program, wherein the current activity is one of the plurality of activities associated with the first service;

select a first user interface of the plurality of user interfaces based on the user interface framework and a combination of: the first service, the first stage, and the current activity;

determine, based on the user interface framework and the combination, one or more data entry fields, of a plurality of data entry fields of the first user interface, that are to be displayed via the task management application, wherein the user interface framework indicates which data entry fields of the plurality of data entry fields are to be displayed based on the combination of the first service, the first stage, and the current activity; and in response to determining the one or more data entry fields that are to be displayed, cause the first user interface comprising the one or more data entry fields to be displayed by the task management application, wherein the remaining data entry fields, of the plurality of data entry fields of the first user interface, are not displayed via the task management application based on the user interface framework and the combination of the first service, the first stage, and the current activity.

20. The system of claim 19, wherein the program is a therapy, the first service is associated with patient acquisition of the therapy, the first stage is associated with completion of the first service, and the current activity is associated with completion of the first stage.

* * * * *